(12) United States Patent
Norton et al.

(10) Patent No.: US 9,011,319 B2
(45) Date of Patent: Apr. 21, 2015

(54) CONICAL LAPAROSCOPIC APPARATUS FOR MINIMALLY INVASIVE SURGERY

(75) Inventors: Michael J. Norton, Tyler, TX (US); Noel D. Ischy, Tyler, TX (US)

(73) Assignee: Axcess Instruments, Inc., Tyler, TX (US)

( * ) Notice: Subject to any disclaimer, the term of this patent is extended or adjusted under 35 U.S.C. 154(b) by 233 days.

(21) Appl. No.: 12/220,248

(22) Filed: Jul. 23, 2008

(65) Prior Publication Data
US 2009/0012477 A1 Jan. 8, 2009

Related U.S. Application Data

(63) Continuation-in-part of application No. 11/710,388, filed on Feb. 23, 2007.

(60) Provisional application No. 60/779,136, filed on Mar. 3, 2006, provisional application No. 60/961,802, filed on Jul. 24, 2007, provisional application No. 60/965,404, filed on Aug. 20, 2007, provisional application No. 61/124,066, filed on Apr. 14, 2008.

(51) Int. Cl.
*A61B 1/313* (2006.01)
*A61B 1/018* (2006.01)
*A61B 17/34* (2006.01)

(52) U.S. Cl.
CPC ......... *A61B 17/3423* (2013.01); *A61B 17/3421* (2013.01); *A61B 17/3474* (2013.01); *A61B 2017/3419* (2013.01); *A61B 2017/3429* (2013.01); *A61B 2017/3445* (2013.01); *A61B 2017/3447* (2013.01); *A61B 2017/3466* (2013.01); *A61B 2017/3484* (2013.01); *A61B 2017/3492* (2013.01)

(58) Field of Classification Search
CPC ..................... A61M 25/02; A61M 2025/0286; A61M 2025/2025; A61M 2025/0293; A61B 19/10; A61B 19/24; A61B 2019/38; A61B 17/3423; A61B 2017/3425; A61B 2017/3427; A61B 2017/3429; A61B 2017/3445; A61B 2017/3466; A61B 2017/3484; A61B 2017/3492
USPC .......... 604/539, 174, 164.04; 600/114; 6/539, 6/174, 164.04
See application file for complete search history.

(56) References Cited

U.S. PATENT DOCUMENTS

| | | | |
|---|---|---|---|
| 4,895,561 A | * | 1/1990 | Mahurkar ........................ 604/43 |
| 5,183,471 A | | 2/1993 | Wilk |
| 5,269,772 A | | 12/1993 | Wilk |
| 5,507,758 A | | 4/1996 | Thomason et al. |
| 5,569,205 A | | 10/1996 | Hart et al. |

(Continued)

*Primary Examiner* — Kathleen Holwerda
*Assistant Examiner* — Sarah W Aleman (57) ABSTRACT

A single body port or body flange access device having an oval shape and associated stabilizer anchor for performing laparoscopic surgery is disclosed. The device is slipped into the body anchor stabilizer first so that the anchor stabilizer lifts up fat and peritoneum inside the body thereby keeping the operating area clear and acting to hold the body flange in place. The device further has a plurality of crisscrossing conduits assuming the shape of a cone through which surgical instruments may be inserted. The instruments are manipulated so that triangulation is obtained using one patient body flange while standard surgical procedures are performed on the patient. Due the oval shape of the device, the device minimally rotates while instruments are manipulated.

13 Claims, 10 Drawing Sheets

(56) References Cited

U.S. PATENT DOCUMENTS

| | | |
|---|---|---|
| 6,066,090 A | 5/2000 | Yoon |
| 6,086,603 A * | 7/2000 | Termin et al. ............ 606/191 |
| 6,277,064 B1 | 8/2001 | Yoon |
| 6,440,061 B1 | 8/2002 | Wenner et al. |
| 6,454,783 B1 | 9/2002 | Piskun |
| 6,508,759 B1 * | 1/2003 | Taylor et al. ............ 600/168 |
| 6,551,270 B1 * | 4/2003 | Bimbo et al. ............ 604/93.01 |
| 6,648,816 B2 | 11/2003 | Irion et al. |
| 6,669,674 B1 * | 12/2003 | Macoviak et al. ............ 604/264 |
| 6,916,331 B2 * | 7/2005 | Mollenauer et al. ............ 606/213 |
| 7,753,901 B2 * | 7/2010 | Piskun et al. ............ 604/539 |
| 2003/0004520 A1 * | 1/2003 | Haarala et al. ............ 606/108 |
| 2004/0167543 A1 * | 8/2004 | Mazzocchi et al. ............ 606/130 |
| 2005/0251144 A1 | 11/2005 | Wilson et al. |
| 2007/0208312 A1 | 9/2007 | Norton et al. |

\* cited by examiner

PRIOR ART

CONICAL LAPAROSCOPIC APPARATUS FOR MINIMALLY INVASIVE SURGERY

This application is a continuation-in-part of U.S. patent application Ser. No. 11/710,388 filed on Feb. 23, 2007 claiming the benefit of priority of U.S. Provisional Application Ser. No. 60/779,136, filed on Mar. 3, 2006, and further claims benefit of priority of U.S. Provisional Application 60/961,802, filed on Jul. 24, 2007, U.S. Provisional Application 60/965,404, filed on Aug. 20, 2007, and U.S. Provisional Application 61/124,066 filed on Apr. 14, 2008.

TECHNICAL FIELD OF THE INVENTION

This device and method relate to laparoscopic surgical procedures and in particular to an improved device and method for minimally invasive surgical procedures.

BACKGROUND OF THE INVENTION

Minimally invasive surgery has improved patient care by decreasing pain, shortening hospital stays, offering a faster recovery time and much smaller scars. In fact the surgical procedure is much shorter than standard procedures and offers less chance of infection, etc. These laparoscopic procedures are proving popular with the patient.

During minimally invasive procedures for the abdominal surgeries such as:
 laparoscopic appendectomy (removal of the appendix);
 laparoscopic cholecystectomy (removal of the gallbladder);
 laparoscopic colectomy (removal of part or all of the colon);
 laparoscopic fundoplication (corrects severe or persistent acid reflux);
 laparoscopic hysterectomy (removal of the uterus); or
 laparoscopic ventral hernia repair (repair of an abnormal bulging of the abdominal wall often at the site of a previous surgical incision),
the surgeon makes a series of three to five small, dime-sized incisions in the patient's abdomen. Carbon dioxide gas is used to inflate the abdomen and create a working space between the internal organs and the skin. A small video camera, or scope, then is placed in one of the incisions, providing the surgeon with a magnified view of the patient's internal organs on a television monitor in the operating room. In some procedures, like MIP for colon conditions, a slightly larger incision may be needed.

Thus, the procedure requires body access devices, which are utilized to introduce visualization equipment and operative instruments rather than a standard incision to access a required part of the body. Nonparallel instrumentation is necessary to create a "depth of field" (3-dimensional vision) and introduce a variety of instrumentation. This concept is commonly known as triangulation.

In the past multichannel devices have been used by the surgeon using narrow parallel channels (within the single multichannel access device). These narrow parallel channels have been found to limit the field of view and reduce depth perception. Thus, multichannel devices have not met the needs of the surgical community and are rarely used.

Nonparallel multiple access devices would allow the surgeon to introduce numerous types of instruments with triangulation through one body access opening. This concept would preserve triangulation and create the required field and depth of view while allowing the surgeon to utilize one body flange for multiple simultaneous tasks, which would be required to complete an operation on any applicable body area or space.

The current state of the art utilizes entry devices (body flanges) that have a similar cross-section as a silver dollar and incorporate a control head (gas in fusion port and sealing systems for insertable surgical instruments that have almost double cross-section as the part of the flange that attaches to the abdominal wall or body entry port. This means that large incisions will be used when operating on obese patients to allow for the large control head.

Wilk in U.S. Pat. No. 5,183,471 discloses a "Laparoscopic Cannula" that has a central conduit with a side crossing conduit that passes through the central conduit thereby creating an obstacle within the central conduit. The disclosure teaches a means to facilitate the temporary insertion of an extra laparoscopic instrument without having to make another perforation of the abdomen. The side crossing conduit will require that the central conduit be large; otherwise, a standard instrument would not be able to pass through the central conduit. The central conduit will allow a surgical instrument to "look" vertically downward over the operation point while the side crossing conduit will pass an instrument to one side of the operation point. Wilk continues to teach a second body flange for illumination and vision and does not discuss triangulation.

Wilk in U.S. Pat. No. 5,269,772 discloses a "Laparoscopic Cannula Assembly and Associated Method" which essentially is two parallel swiveling conduit passing through the same body opening and is a continuation-in-part of his '471 disclosure examined above. The parallel conduits do not cross over each other; however, the device will allow one instrument to be to one side of the operation point while the other instrument may be to the other side. The swiveling assembly will require a rather large opening in the abdomen wall. As in his '471 disclosure, he continues to teach a second body flange for illumination and vision and does not discuss triangulation.

Yoon in U.S. Pat. No. 6,066,090 discloses a "Branched Endoscope System" which discusses a single body flange having a plurality of tubes passing through the conduit for various surgical instruments. Yoon shows an embodiment in which the inside section of the body flange splits in two parts each having a bend thereby allowing a tube to overlook the other tube. The Yoon '090 device is designed to pass through the current art body flange having a single conduit.

Yoon in U.S. Pat. No. 6,277,064 discloses a "Surgical Instrument with Rotatably Mounted Offset Endoscope." The apparatus is a variation of the '090 device and is designed to pass through the current art body flange having a single conduit.

Wenner et al. in U.S. Pat. No. 6,440,061 disclose a "Laparoscopic Instrument System for Real-Time Biliary Exploration and Stone Removal." This device has multiple ports within its system, but, like Yoon, is designed to pass through the current art body flange having a single conduit.

Bimbo et al. in U.S. Pat. No. 6,551,270 disclose a "Dual Lumen Access Port." The device is essentially a current state of the art body flange with parallel entry ports that open into a single conduit which will accept two surgical tools through one body flange without ensuring a three dimensional field of view. Bimbo teaches multiple instruments through a single conduit but does not explore the concept of a single body flange replacing surgical procedures using multiple body flanges.

Piskun in U.S. Pat. No. 6,454,783 discloses "Laparoscopic Instruments and Trocar Systems for Trans-umbilical Laproscopic (sic) Surgery." Piskun discloses an instrument system that markedly increases the work space between the hands of the surgeon. The system includes s-shaped laparoscopic tools and associated curved trocars (sealable conduit passing through the umbilicus). The disclosure goes further to propose at least one curved trocar contained within an inflatable unit for placement through the umbilicus—essentially an inflatable body flange.

The inventors in their earlier application, of which this is a continuation-in-part, disclosed a body flange or body anchor system which provided an apparatus and method that would allowed the surgeon to perform minimally invasive operations with body flanges having a smaller overall cross-section while allowing for triangulation within the patient. Such a device and method will result in fewer incisions for body access openings thus further decreasing the pain caused by surgery and further decreasing the recovery time and further reducing the risk of infection. However, as their device was developed it was discovered that a perfectly round shape tended to swivel in the umbilicus and tended to lift out of the umbilicus in spite of the sutures.

It was discovered that if the shape of the anchor was modified to be oval in shape then the anchor would not as easily rotate. At the same time it was discovered that if a stabilizer extension (shaped somewhat like the toe of a boot) was added to the lower inside part of the anchor the tendency to lift out of the umbilicus was further reduced. The stabilizer extension added one further advantage to the body anchor in that it tended to elevate fat and peritoneum inside the patient's body thereby keeping the internal opening clear for surgical instruments.

During further experimentation with the crisscrossed anchor employing the "boot" stabilizer, it was discovered that a substantial improvement in the ease of instrument positioning with the body cavity would occur if the conduit passages were "bored-out" into the shape of a cone either above or below the point in the anchor where it passes into the body. As a part of this discovery, it was noted that the conical conduit must be angled away from each other substantially like bicycle spokes while maintaining a crisscross pattern (for three-dimensional viewing) resulting in trajectories that may be nonparallel or parallel which may of may not crisscross within the actual anchor itself.

Further development lead to a concept to allow for a fourth conduit about the outside of the anchor without significantly increasing the "diameter" of the anchor. At the same time it was realized that if the conduit passages were made of a flexible material, then the overall triangulation could be substantially increased.

SUMMARY OF THE INVENTION

The invention consists of a "body flange" or "trans-axis-uniport" ("TAU") which is anchored to the body with a standard suture anchoring points or a twin hexagonal tie-down. In turn, the body anchor contains a crisscrossed plurality of conduits which allow nonparallel introduction of equipment and/or instruments. The conduits may be parallel, nonparallel, straight or curved, but enter the body through one body opening. (It may be necessary during some procedures to have additional body openings.)

Rather than use the current art round body flange shape, the device is slightly oval (or elliptical if viewed from beneath). In a further embodiment the perimeter of the flange at the point inside the body is less than the perimeter outside the body thereby providing a further circumferential oval shape. A stabilizer extension shaped somewhat like the toe of a boot is added to the lower (inside the body) perimeter of the flange. The stabilizer extends along an axis that joins the foci of the ellipse.

The conduit extending through the anchor are "bored-out" or enlarged either preferably above the point in the anchor where it passes through the body or below the point. This allows the surgical instrument to freely move back and forth within the body (in a circular pattern) thereby increasing the "fulcrum" (movement of the instrument tip) within the body. In an alternate version the conical shapes of the conduit are combined into one cone which follows the outside conical shape of the anchor. A rubberized-malleable seal is placed within the cone or cones of the conduit and in one alternate the seals may be placed at the bottom (inside the patient) side of the anchor. The bottom placement of seals allows for more freedom of movement of the surgical instruments and removes the chance of seal bumping against one another.

DESCRIPTION OF THE PREFERRED EMBODIMENT

In reading this disclosure, the reader should understand that the term body flange generally means the entire device used to temporarily seal an incision in a patient. Thus, the body flange would include the body anchor—the section of the device that fits within the abdominal wall and is temporarily sutured to the abdominal lining, any passageways extending through the body anchor (both above and below), any seals or other apparatus that is required to form the complete temporary entry closure.

Figure 1:
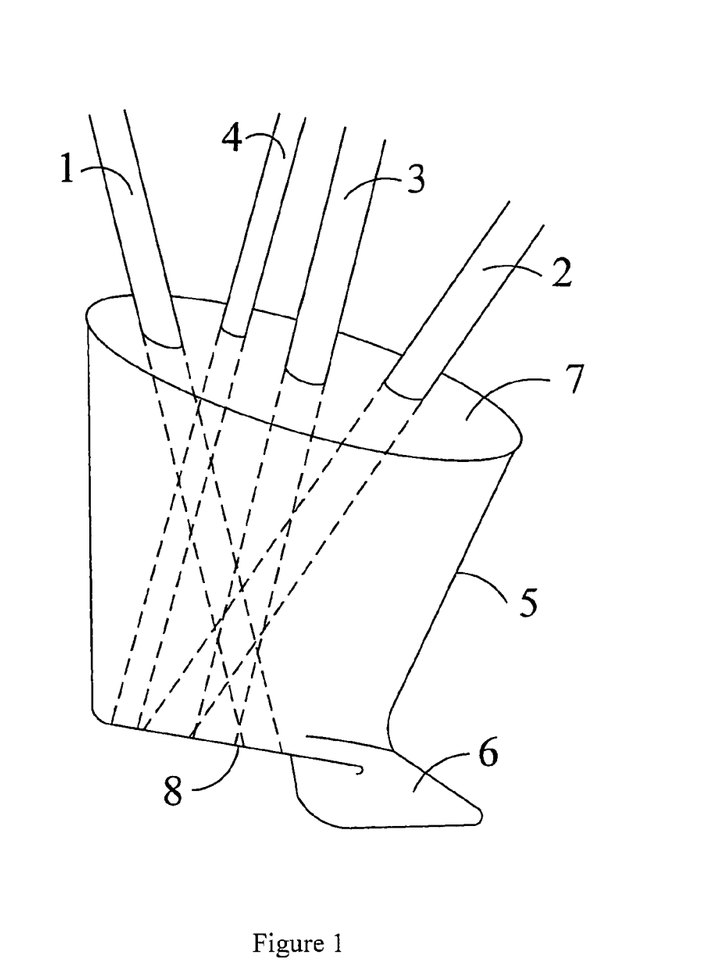
FIG. 1 shows isometric view of the body anchor of the instant invention showing how the conduit apertures cross over (criss-cross) within the anchor and showing the anchor stabilizer.

Turning now to FIG. 1, the improved body anchor is shown as item 5. The overall shape is somewhat like a boot, in that the upper perimeter, 7, and lower perimeter, 8 are elliptical. The anchor stabilizer, 6, extends from the lower perimeter following an axis which passes through the foci of the elliptical lower perimeter, 8. Crisscrossing instrument conduit, 1 and 2 are shown. It should be noted that these conduit need not crisscross to take advantage of the improved body anchor utilizing the defined shapes and stabilizer and in fact such condition would be an alternate embodiment. A further straight conduit, 3, is shown passing behind the crisscrossing conduit as is an inflation passage, 4.

Figure 2:
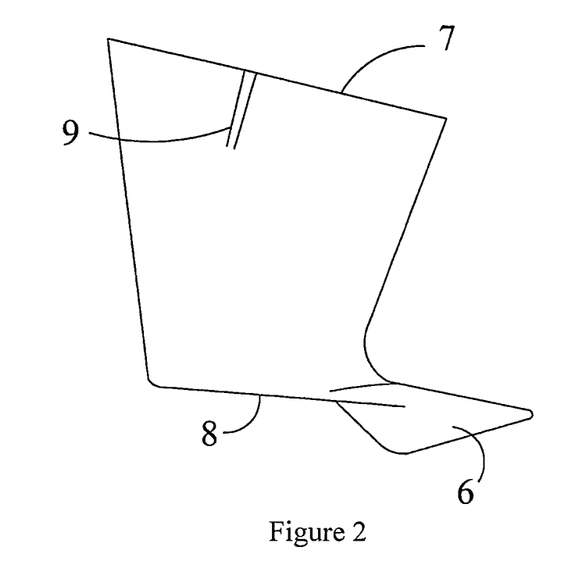
FIG. 2 shows a side view of the instant invention.
Figure 3:
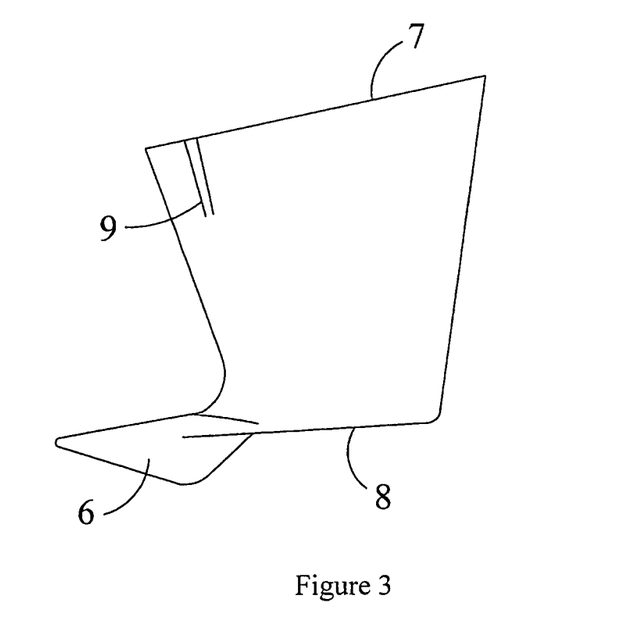
FIG. 3 shows a side view of the instant invention rotated 180-degrees from the illustration in FIG. 2.

It should be noted that the oval shaped body flange and stabilizer can function with only one conduit and the illustration of FIG. 1 must not be construed to require a plurality of conduit; thus, the illustration of FIG. 1 should not be construed as a limitation. FIGS. 2 and 3 serve to illustrate side views of the improved body anchor further showing and claiming the anchor stabilizer, 6. Also shown is the suture guide, 9.

Figure 4:
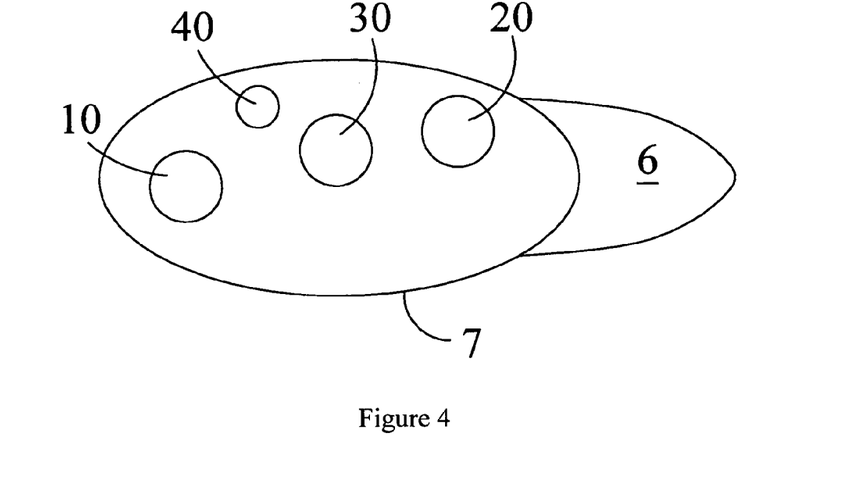
FIG. 4 is a top view of the instant invention
Figure 5:
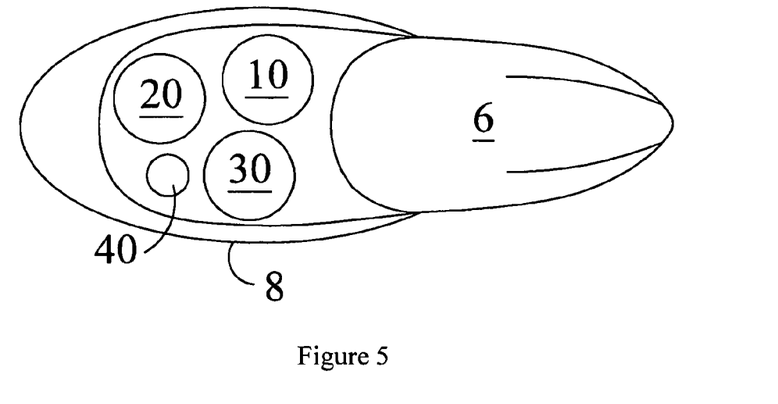
FIG. 5 is a bottom view of the instant invention.

Likewise FIGS. 4 and 5 are top and bottom views of the improved body anchor further showing and claiming the anchor stabilizer, 6.

Figure 6:
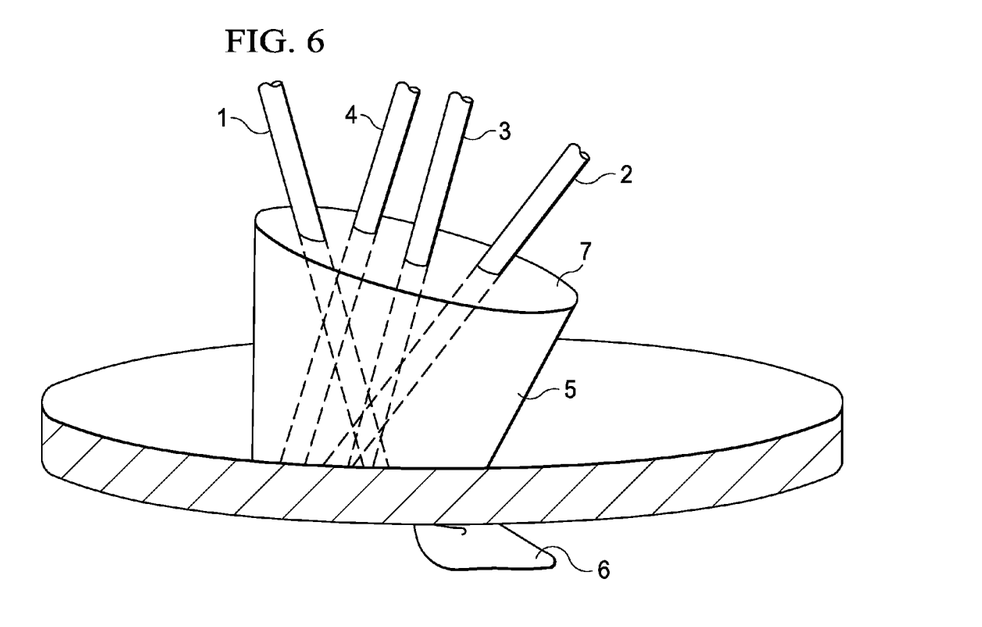
FIG. 6 shows a side view of the instant device in place within the body of the patient illustrating how the anchor stabilizer functions.

FIG. 6 shows the device in place within the body of a patient and clearly illustrates how the anchor stabilizer acts to hold the anchor in place while lifting fat and peritoneum within the body.

Figure 7:
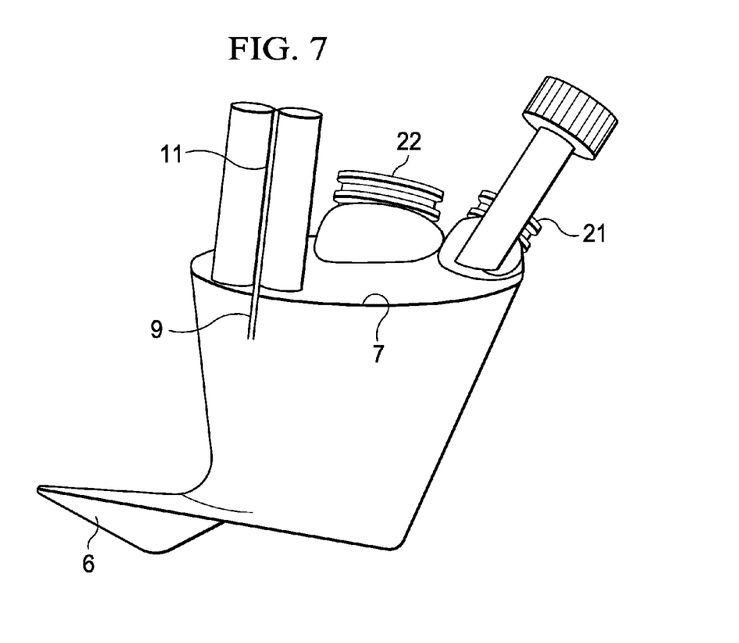
FIG. 7 shows a twin hexagonal suture tie-down.

FIG. 7 shows the twin hexagonal suture anchor 11 (or tie-down point). This set of twin posts 11 could be flat (to each other), triangular (with the apex of each triangle touching), round, or possibly any geometric shape. The tie-down point operates very simply by tightly holding the suture between the two posts 11. The preferred shape is hexagonal, but an octagonal shape may also be employed. Also shown in FIG. 7 are two conduits with standard "outer" seals, 21 and 22. That is to say the seal between the surgical instrument and the conduit is standard and is located "outside" the conduit. Compare this concept to a further improvement to be described below.

Figure 8:
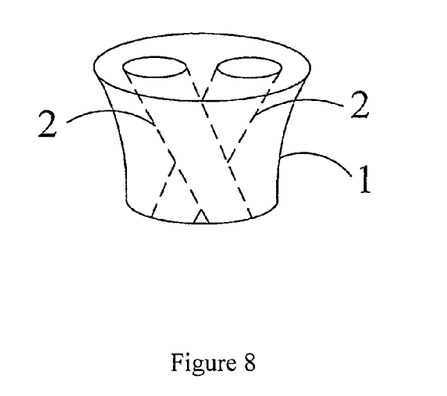
FIG. 8 shows the art disclosed in an earlier application by the inventors on which this application continues in part.

FIG. 8 shows the prior art multi-channel body flange, 1', described in the inventors' parent application Ser. No. 11/710,388 and illustrating two crisscrossing conduit, 2'.

Figure 9:
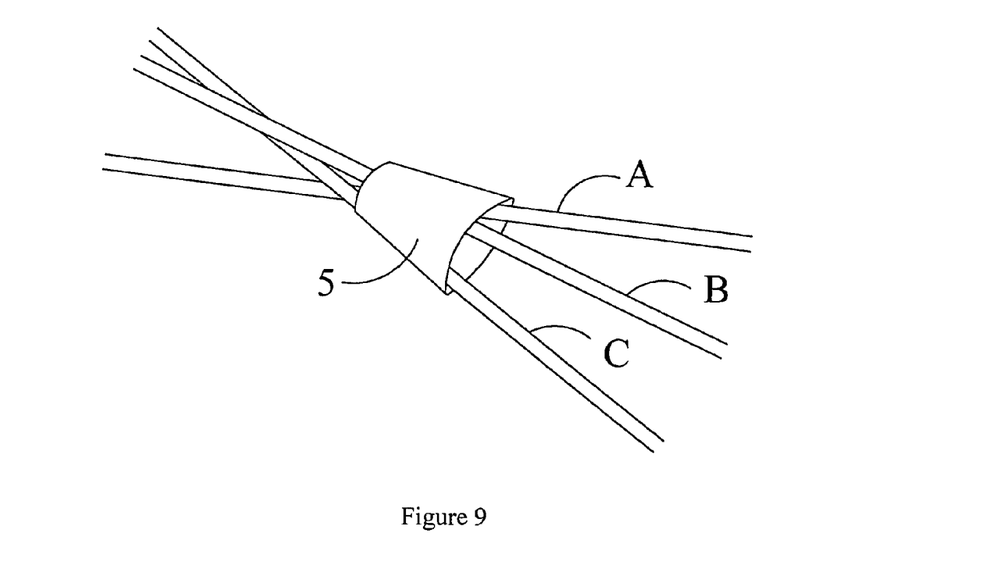
FIG. 9 identifies three simulated instruments (as A, B, and C) and indicating where (in this case within the device) the crisscross occurs.
Figure 10:
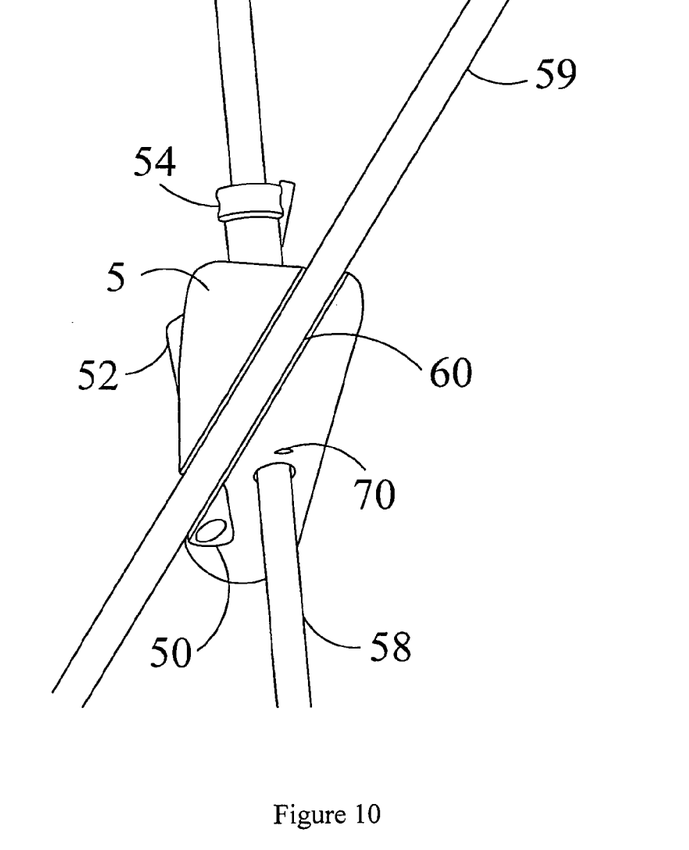
FIG. 10 is a side view of the further improved anchor showing two simulated instruments crisscrossing, one inside the anchor and the other outside the anchor, but still positioned by the anchor.

FIG. 9 shows the conical form of the crisscrossing conduit with three simulated instruments passing through the body flange, 5. The figure shows clearly the "bicycle-spoke" arrangement that the surgical instruments, A, B, and C, will assume when passing through the body flange. The instruments may now be readily and easily manipulated over a large arc within the body while maintaining the critical three-dimensional view.

FIGS. 10 through 14 show additional embodiments of the instant device. An external crisscross passage, 60, has been placed in the outer wall of the body anchor, 5. A simulated surgical instrument, 59, is shown passing through the passage. There is no seal shown, however, flexible rubber may be placed in the passage, which would seal against the instrument: the human body will provide the remaining seal. Also shown is the air inflation passage, 70.

Figure 11:
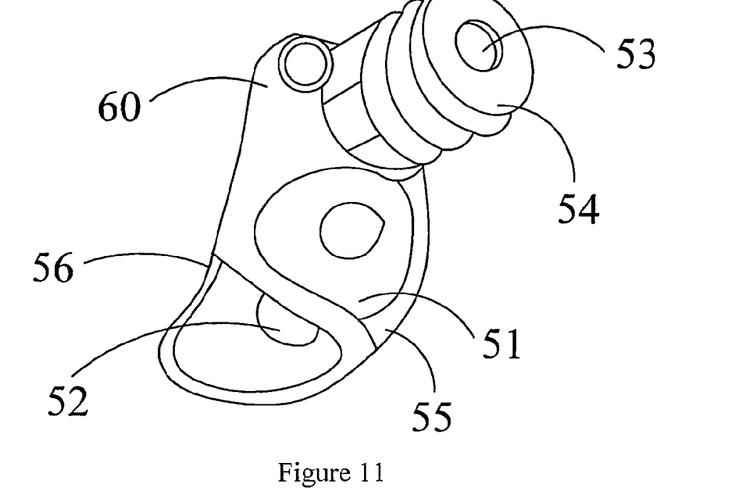
FIG. 11 is a top view of the further improved anchor showing four conduit, two utilizing a flexible wall (with seals at the bottom), one using a fixed conduit (with a normal seal) and one passing through the edge of the anchor. Also shown is an inflation conduit.

FIG. 11 shows the inside crisscrossing conduit, 51 and 52. It would be possible to slightly enlarge these conduits to assume the conical shape; however, this may result in a large (overall) diameter flange. Note the flexible external membranes in these conduits, 55 and 56. If and when the surgeon manipulates the instruments within these conduits and needs more movement, the two flexible walls will distend.

Figure 12:
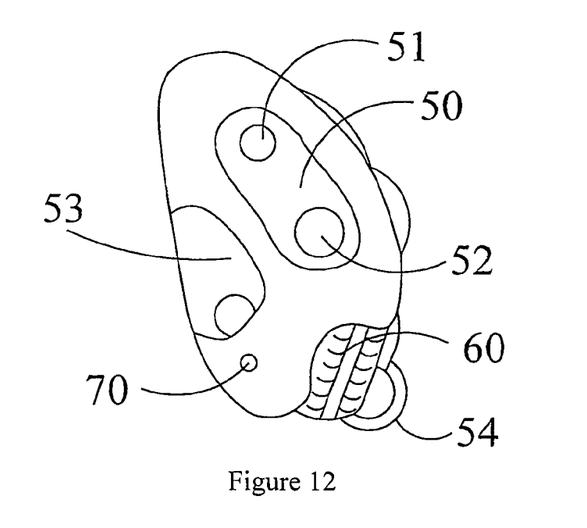
FIG. 12 is a bottom view of the further improved anchor clearly showing the two lower seals, the fixed conduit exit, the side channel and the inflation opening.

FIG. 12 clearly shows the instrument seal, 50, placed on the bottom of the body flange (the bottom being defined as the portion of the anchor which is fully within the patient). This dual seal serves to seal passages, 51 and 52. An alternate (standard) seal, 54, is shown on passage 53. The standard seal on passage 53 may be replaced with a bottom seal as shown by seal 50.

Figure 13:
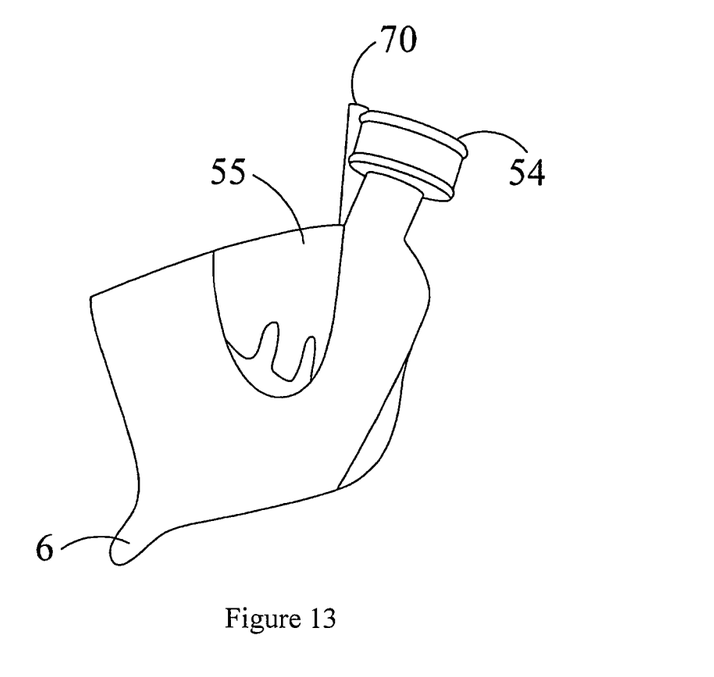
FIG. 13 is a side view of the further improved anchor showing the flexible side.
Figure 14:
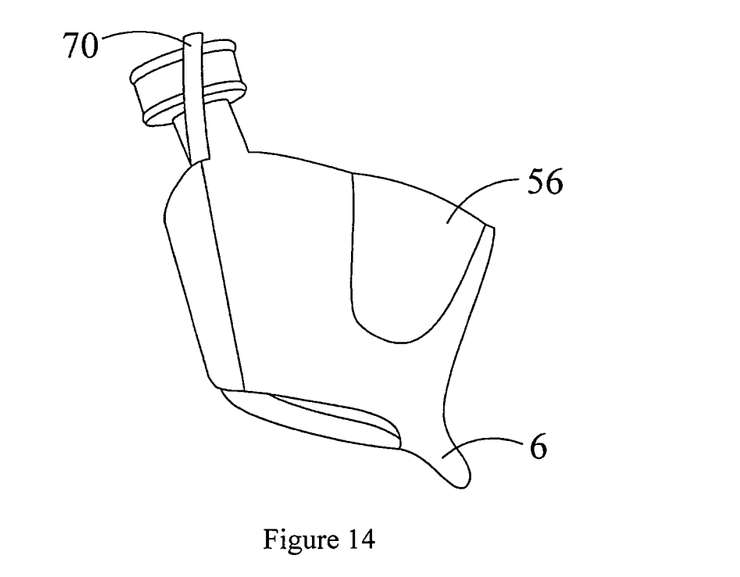
FIG. 14 is the same as FIG. 13, but rotated 180-degrees.
Figure 15:
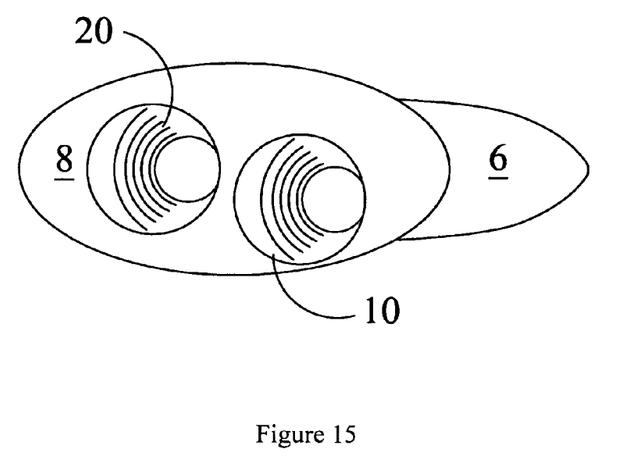
FIG. 15 is a top view of the instant invention of FIG. 5, showing the how the apertures are bored out to take a conical shape.
Figure 16:
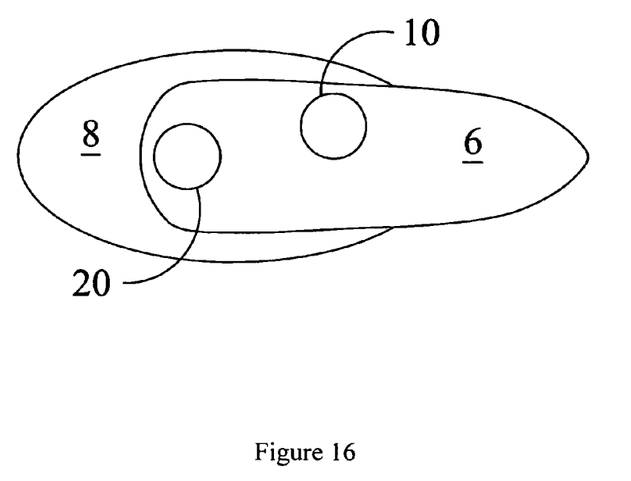
FIG. 16 is a bottom view of the instant invention of FIG. 16 further showing the conical shape of the apertures.
Figure 17:
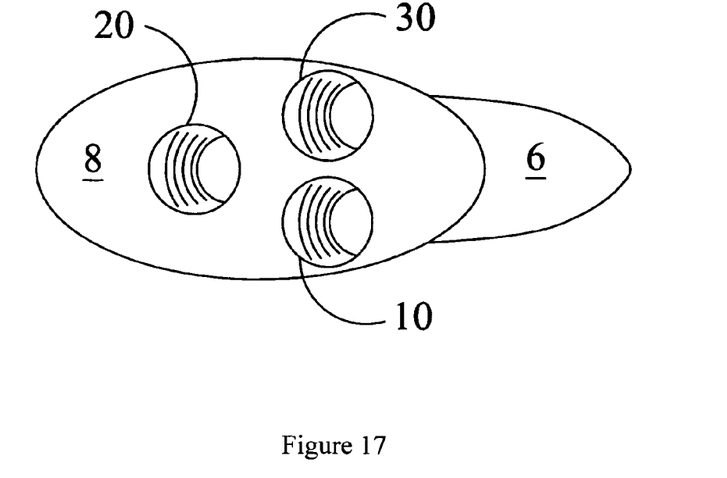
FIG. 17 is a top view of the instant invention of FIG. 5, but with three apertures showing how the apertures are bored out to take a conical shape.
Figure 18:
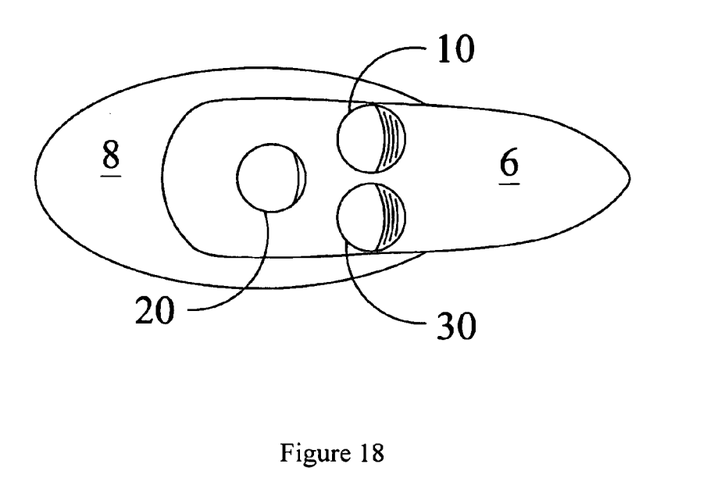
FIG. 18 is a bottom view of the instant invention of FIG. 16 further showing the conical shape of the apertures.

As seen in FIGS. 13 and 14, the anchor stabilizer 6 is located at the lower exit end and extends laterally and outwardly from the conical shaped body and beyond a perimeter of the upper access surface 7, as seen in FIG. 7. The anchor stabilizer 6 has a fulcrum structure that circumscribes the conical shaped body by less than 90 degrees.

It is the intent of the invention to reduce the overall body incision, thus the body flange of the instant invention (at the point where it is designed to penetrate the abdominal wall) to a minimum. Note that, as the instruments are manipulated within the flange, the instrument trajectories may range from nonparallel to parallel crisscrossing. The device is shown with a US dime for size comparison.

In the current series of prototype model body flanges, the overall (penetration point) diameter is about 15 mm and allows for three instruments having diameters of 5, 5, and 3 mm respectively. Another prototype has been developed that allows for laparoscopic spleen surgery using instruments having diameters of 5, 5, and 12 (stapler) mm respectively. The overall diameter of this prototype is about 20 mm.

Because the instant devices are smaller (both in diameter and depth) over the current art, the body flange will easily accept flexible instruments, inflexible instruments, curved, straight, instruments with angled lenses, and etc.

We claim:

1. A multiple access body uniport for performing minimally invasive laparoscopic surgery on a body, comprising:
    a one-piece body anchor defined by a longitudinal length and an upper surface and a lower surface, wherein:
        a perimeter of said upper surface is larger than a perimeter of said lower surface;
        at least two surgical passageways are located through said one-piece body anchor and terminate at an entrance aperture on said upper surface of said one-piece body anchor and at an exit aperture on said lower surface of said one-piece body anchor;
        a perimeter of said entrance aperture is larger than a perimeter of said exit aperture;
        said at least two surgical passageways crisscross each other within said body anchor; and
        an anchor stabilizer located at said lower surface and having an upper surface extending outwardly from only a portion of said perimeter of said lower surface of said one-piece body anchor and beyond said perimeter of said upper surface.

2. The one-piece body anchor of claim 1, further comprising a seal located in any of said at least two surgical passageways.

3. The one-piece body anchor of claim 2, wherein said seal is located at said entrance aperture.

4. The one-piece body anchor of claim 2, wherein said seal is located at said exit aperture.

5. The one-piece body anchor of claim 2, wherein said seal is a dual seal located at said entrance and said exit aperture.

6. The one-piece body anchor of claim 1, wherein said at least two surgical passageways receive a surgical instrument therein.

7. The one-piece body anchor of claim 1, wherein one of said at least two surgical passageways is configured to receive a laparoscopic camera therethrough.

8. The one-piece body anchor of claim 1, further comprising a separate air inflation passageway for insufflation of said body.

9. The one-piece body anchor of claim 8, wherein said air inflation passageway includes a seal located at an entrance, exit, or both of said air inflation passageway.

10. The one-piece body anchor of claim 1, further comprising a seal structure that extends above said upper surface for at least one of said at least two surgical passageways, said seal structure having an access opening located on an access end thereof and including a seal located about said access opening.

11. The one-piece body anchor of claim 1, wherein said upper surface is a flat surface and a lower surface of said anchor stabilizer is a convex surface.

12. The one-piece body anchor of claim 1, further comprising a suture guide fat led in said upper surface.

13. The one-piece body anchor of claim 12, wherein said suture guide comprises and is located between a pair of posts extending upwardly from said upper surface.

* * * * *

UNITED STATES PATENT AND TRADEMARK OFFICE
CERTIFICATE OF CORRECTION

| | | |
|---|---|---|
| PATENT NO. | : 9,011,319 B2 | Page 1 of 1 |
| APPLICATION NO. | : 12/220248 | |
| DATED | : April 21, 2015 | |
| INVENTOR(S) | : Michael J. Norton et al. | |

It is certified that error appears in the above-identified patent and that said Letters Patent is hereby corrected as shown below:

In the Claims:

Column 7, Line 23, Claim 12, please replace --fat let-- with --formed--

Signed and Sealed this
Twenty-ninth Day of September, 2015

Michelle K. Lee
*Director of the United States Patent and Trademark Office*